United States Patent
Ayanruoh

(10) Patent No.: US 6,381,484 B1
(45) Date of Patent: Apr. 30, 2002

(54) PALM SIZED MEDICAL EXAMINATION DEVICE

(76) Inventor: Steve T Ayanruoh, 115 Eisenhower Dr., Yonkers, NY (US) 10710

(*) Notice: Subject to any disclaimer, the term of this patent is extended or adjusted under 35 U.S.C. 154(b) by 0 days.

(21) Appl. No.: 09/351,451

(22) Filed: Jul. 12, 1999

(51) Int. Cl.[7] .................................................. A61B 5/05
(52) U.S. Cl. ...................................................... 600/407
(58) Field of Search ................................. 600/381, 407, 600/446, 478, 109, 160, 476, 300, 301; 128/920, 897, 898; 705/3

(56) References Cited

U.S. PATENT DOCUMENTS

| | | | |
|---|---|---|---|
| 5,311,859 A | * 5/1994 | Monroe et al. | 600/112 |
| 5,363,839 A | * 11/1994 | Lankford | 600/112 |
| 5,468,947 A | * 11/1995 | Danielson et al. | 235/472 |
| 5,558,638 A | * 9/1996 | Evers et al. | |
| 5,701,904 A | * 12/1997 | Simmons et al. | 600/301 |
| 5,827,179 A | * 10/1998 | Lichter et al. | |
| 5,885,214 A | * 3/1999 | Monroe et al. | 600/407 |
| 6,151,581 A | * 11/2000 | Kraftson et al. | |
| 6,163,281 A | * 12/2000 | Torch | 341/21 |
| 6,171,112 B1 | * 1/2001 | Clark et al. | |
| 6,192,266 B1 | * 2/2001 | Dupree et al. | |
| 6,200,531 B1 | * 2/2001 | Liljestrand et al. | |
| 6,201,993 B1 | * 3/2001 | Kruse et al. | |

* cited by examiner

Primary Examiner—Brian L. Casler
(74) Attorney, Agent, or Firm—Michael I. Kroll

(57) ABSTRACT

A hand held medical examination device for performing a physical examination on a patient. The hand held medical examination device includes a hand held computer including a microprocessor, a touch screen for inputting data to the microprocessor, a display screen and a connection port. A cable wire is connected to the microprocessor through the connection port and includes a universal adapter for connection to any one of a plurality of medical devices used to perform a physical examination. A camera extends through the cable wire for capturing an image viewed through the medical device connected to the universal adapter and provides data related to the captured image to the microprocessor for processing and display on the display screen. A memory unit is connected to the microprocessor for storing data input from the keyboard and camera related to a plurality of patients. The touch screen displays prompts for inputting data to the microprocessor in accordance with a software program stored in memory. The hand held medical examination device may also be provided along with a peripheral device port for connecting the microprocessor to a peripheral device. The plurality of medical devices which may be connected to the universal adapter include an ear piece, a pair of eye glasses, a tongue depressor and electrocardiogram probes.

12 Claims, 7 Drawing Sheets

PALM SIZED MEDICAL EXAMINATION DEVICE

BACKGROUND OF THE INVENTION

1. Field of the Invention

The present invention relates generally to medical devices and, more specifically, to a palm sized device able to store data regarding a patient and connect with various medical devices for displaying images viewed through the medical devices on a display screen thereby aiding a medical technician in performing an examination.

2. Description of the Prior Art

Numerous types of devices for aiding in the performing a medical examination have been provided in the prior art. For example, U.S. Pat. Nos. 4,756,304; 5,437,626; 5,468,947; 5,739,665 and 5,778,882 all are illustrative of such prior art. While these units may be suitable for (lie particular purpose to which they address, they would not be as suitable for the purposes of the present invention as heretofore described.

U.S. Pat. No. 4,756,304

Inventor: Robert S. Watanabe

Issued: Jul. 12, 1988

An arthroscopic video camera system especially constructed to utilize a compact miniature CCD chip type of color video camera for high resolution and high light sensitivity. A disposable sterile plastic housing is provided for the camera. Prior to the arthroscopic procedure, the camera is placed in the sterile plastic housing, and is connected through a sterile electric cord to an electronic control unit. A gas sterilized adapter is plugged into an arthroscopic mounting bracket, and a sterilized light cord extending from a remote light source is then plugged into the mounting bracket. Finally, a selected arthroscope is also plugged into the mounting bracket by light from the remote source, and to provide images through the mounting bracket for the video camera.

U.S. Pat. No. 5,437,626

Inventor: Donald Cohen et al.

Issued: Aug. 1, 1995

A shunt for relieving hydrocephalus has a closed distal end and an aperture formed in the distal end. A hollow hypotube has a distal end, and the hypotube holds an image fiber which protrudes beyond the distal end of the hypotube. The hypotube is positioned in the shunt with the distal end of the hypotube abutting the distal end of the shunt and the image fiber protruding through the aperture. The hypotube with shunt can then be advanced into the brain of a patient, while the surgeon views the path of advancement on a nearby video monitor which is connected to the image fiber. In an alternate embodiment, the distal end of the image fiber is flush with the distal end of the hypotube. The shunt has a slit formed in its distal end, and the hypotube with image fiber can be selectively advanced through the slit to view the area of the brain beyond the catheter.

U.S. Pat. No. 5,468,947

Inventor: Arvin D. Danielson

Issued: Nov. 21, 1995

A hand-held processing system wherein a peripheral module may receive therein a computer processor basic module of standardized construction, with a user-immune real-time multi-tasking operating system. Advantageously the peripheral module or computer processor module may include a touch screen or other highly versatile and compact data input/output device adaptable to graphical and/or other input/output modes suitable for different applications, languages and the like.

U.S. Pat. No. 5,739,665

Inventor: Steven John Bares

Issued: Apr. 14, 1998

A portable RF docking station is detachably coupled to a palm-sized computer to provide extended wireless communication through a radio modem and wire line communication through a wire line modem. Both modems are contained inside the docking station and are powered by rechargeable batteries. The docking station includes a housing having a flat platform, a side section that extends vertically upward along a side edge of the platform and a rear section that extends vertically upward along a rear edge of the platform. The housing in combination with a data connector holds the computer and docking station together as one cohesive unit. A four-stage charging circuit maintains the rechargeable battery in a fully charged condition.

U.S. Pat. No. 5,778,882

Inventor: Stephen A. Raymond et al.

Issued: July 1998

A health monitoring system which tracks the state of health of a patient and compiles a chronological health history of the patient uses a multi-parametric monitor which periodically and automatically measures and records a plurality of physiological data from sensors in contact with the patient's body. The data collected is not specifically related to a particular medical condition but, instead, provides the information necessary to derive patterns which are characteristic of healthy patients as well as those who are ill. The data collected is periodically uploaded to a database in which it is stored along with similar health histories for other patients. The monitor is preferably self-contained in a chest strap which is located on the patient's torso, and makes use of a controller which controls sampling of the desired data and storage of the data to a local memory device pending uploading to the database. The more voluminous data collected is reduced and compressed prior to storage in the local memory device. Preferably, much of the monitor circuitry is run intermittently to conserve power. The monitor data is supplemented with subjective data (such as psychological and environmental conditions) collected from the patient using a hand held data input device which runs a program to solicit information from the patient. The subjective data collected is chronologically aligned with the monitor data in the database such that the healthy history of a patient includes both objective and subjective medical data.

SUMMARY OF THE PRESENT INVENTION

The present invention relates generally to medical devices and, more specifically, to a palm sized device able to store data regarding a patient and connect with various medical devices for displaying images viewed through the medical devices on a display screen thereby aiding a medical technician in performing an examination.

A primary object of the present invention is to provide a hand held medical examination device that will overcome the shortcomings of prior art devices, Another object of the present invention is to provide a hand held medical examination device which is able to connect with numerous medical devices for examining multiple body parts of a patient.

A further object of the present invention is to provide a hand held medical examination device including a miniature camera connected to display a body part being examined on a display screen.

A yet further object of the present invention is to provide a hand held medical examination device able to store a plurality of medical histories and examinations.

A further object of the present invention is to provide a hand held medical examination device wherein the numerous medical devices connect to the device through an adapter cable.

A still further object of the present invention is to provide a hand held medical examination device able to provide quick and easy physical examinations of patients in emergency rooms as patients wait to be seen.

An even further object of the present invention is to provide a hand held medical examination device including a touch screen and stylus for inputting data related to a patient being examined according to stored data forms.

Another object of the present invention is to provide a hand held medical examination device that is simple and easy to use.

A still further object of the present invention is to provide a hand held medical examination device that is economical in cost to manufacture.

Additional objects of the present invention will appear as the description proceeds.

A hand held medical examination device for performing a physical examination on a patient is disclosed by the present invention. The hand held medical examination device includes a hand held computer including a microprocessor, a touch screen for inputting data to the microprocessor, a first display screen and a connection port. A cable wire is connected to the microprocessor through the connection port and includes a universal adapter for connection to any one of plurality of medical devices used to perform a physical examination. A camera extends through the cable wire for capturing an image viewed through the medical device connected to the universal adapter and provides data related to the captured image to the microprocessor for processing and display on the first display screen. A memory unit is connected to the microprocessor for storing data input from the touch screen and camera related to a plurality of patients. A second display screen for displaying data input from the display screen may also be provided along with a peripheral device port for connecting the microprocessor to a peripheral device. The plurality of medical devices which may be connected to the universal adapter include an ear piece, a pair of eye glasses, a tongue depressor and electrocardiogram probes.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DESCRIPTION OF THE REFERENCED NUMERALS

Figure 1:
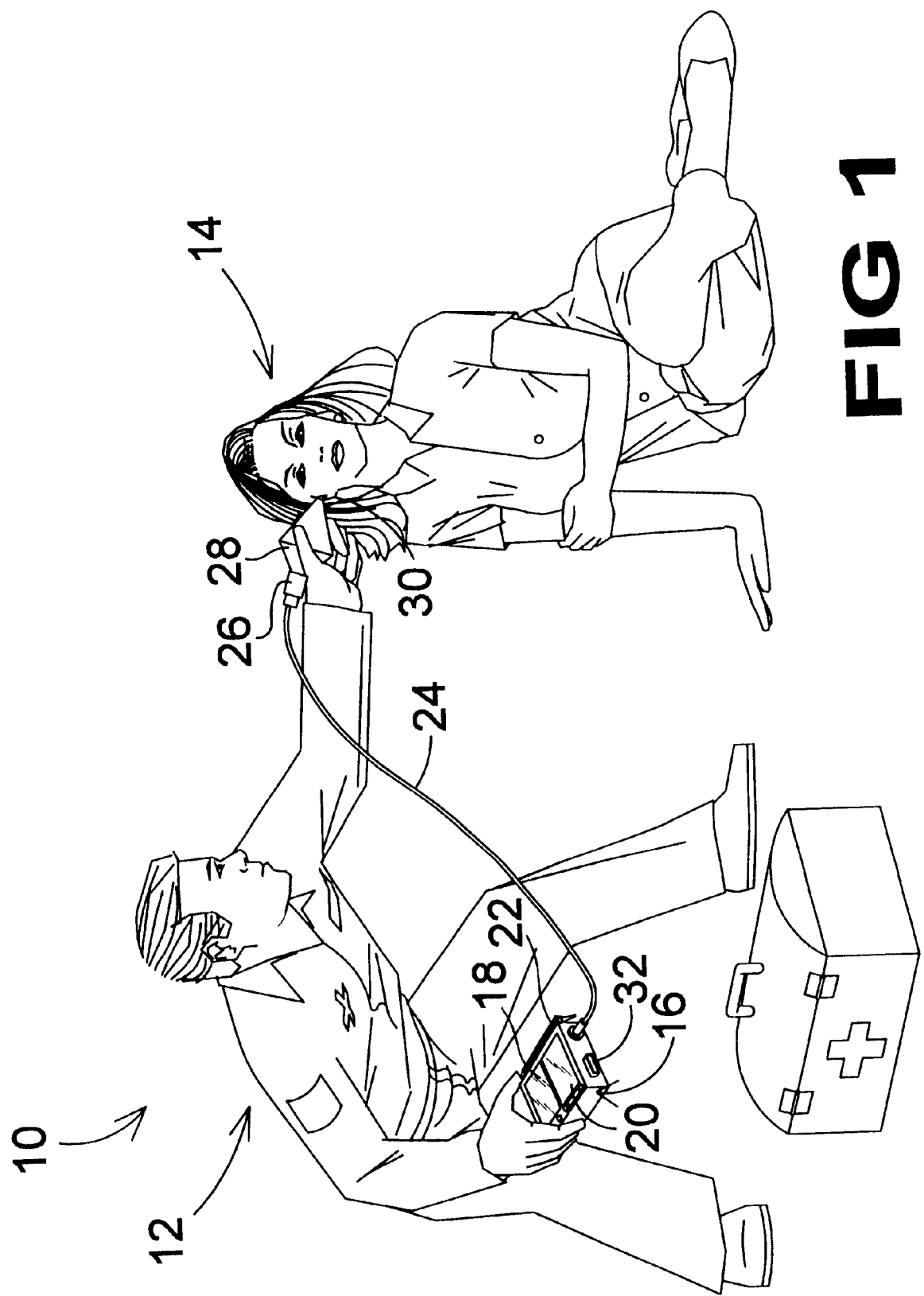
FIG. 1 is a perspective view of the hand held medical examination device of the present invention being used by a medical technician to examine a patient.

Turning now descriptively to the drawings, in which similar reference characters denote elements throughout the several views, the Figures illustrate the hand held medical examination device of the present invention. With regard to the reference numerals used, the following numbering is used throughout the various drawing figures.

10 hand held medical examination device of the present invention
12 medical personnel
14 patient
16 computer
18 image display screen
20 data touch screen
21 power switch
22 stylus for inputting data to touch screen
23 cord for securing stylus to hand held medical examination device
24 fiber optic cable
25 clip on top side of hand held medical examination device for receiving stylus
26 adapter
28 medical device
30 ear of patient
32 printer port
34 side of computer
35 connection port for cable wire
36 printer cable 38 printer
40 adapter for connecting cable wire to computer
42 fiber optic camera
44 medical device for examining ear
45 bulb for insufflating ear drum of patient
46 adapter for connecting medical device for examining ear to cable
48 medical device for examining eye
50 adapter for connecting medical device for examining eye to cable
52 medical device for examining mouth
54 adapter for connecting medical device for examining mouth to cable
56 medical device for taking EKG
58 adapter for connecting medical device for taking EKG to cable
60 microprocessor in computer
62 power source
64 power switch
66 memory
68 external power source

DETAILED DESCRIPTION OF THE PREFERRED EMBODIMENT

Turning now descriptively to the drawings, in which similar reference characters denote similar elements throughout the& several views, FIGS. 1 through 7 illustrate the hand held medical examination device of the present invention indicated generally by the numeral 10.

The hand held medical examination device 10 is illustrated in FIG. 1 being used by a medical technician 12 to perform a physical examination on a patient 14. The medical technician 12 is holding the computer 16 of the hand held medical examination device 10 in one hand. The computer 16 of the hand held medical examination device 10 includes an image display screen 18 for displaying an image viewed by a camera connected thereto, a data display touch screen 20 for displaying data regarding the patient 14 being examined. A stylus 22 is provided for contacting the touch screen 20 and thereby inputting data regarding the patient 14 into the computer 16. A software program is stored within the hand held medical examination device 10 and prompts the medical technician 12 to enter data using the stylus 22 by touching the touch screen 20 at an appropriate location such as according to a check list displayed on the screen 20. The stylus 22 is connected to the hand held medical examination device 10 by a cord 23 and when not in use is received within a clip 25 as can be seen in FIG. 2.

Connected to and extending from the computer 16 is a cable wire 24. The cable wire 24 includes a fiber optic camera extending therethrough for capturing images at which the cable wire 24 is directed and an adapter 26 connected to an end of the cable wire 24 opposite the connection to the computer 16. The fiber optic camera will be discussed hereinafter with specific reference to FIG. 5. The adapter 26 connects with numerous types of medical devices such as the ear piece 28 shown in the figure. When the medical technician 12 places the ear piece 28 up to an ear 30 of the patient 14, the fiber optic camera extending through the cable wire 24 will capture an image for display on the image display screen 18 of the computer 16 thereby providing an enlarged view of the inner ear of the patient 14. The medical technician 12 is then able to input data regarding the displayed image using the keyboard 22. A connection port 32 is provided on a side of the computer 16 for connecting the computer 16 to a printer or other peripheral device in order to output the data stored within the computer 16.

Figure 2:
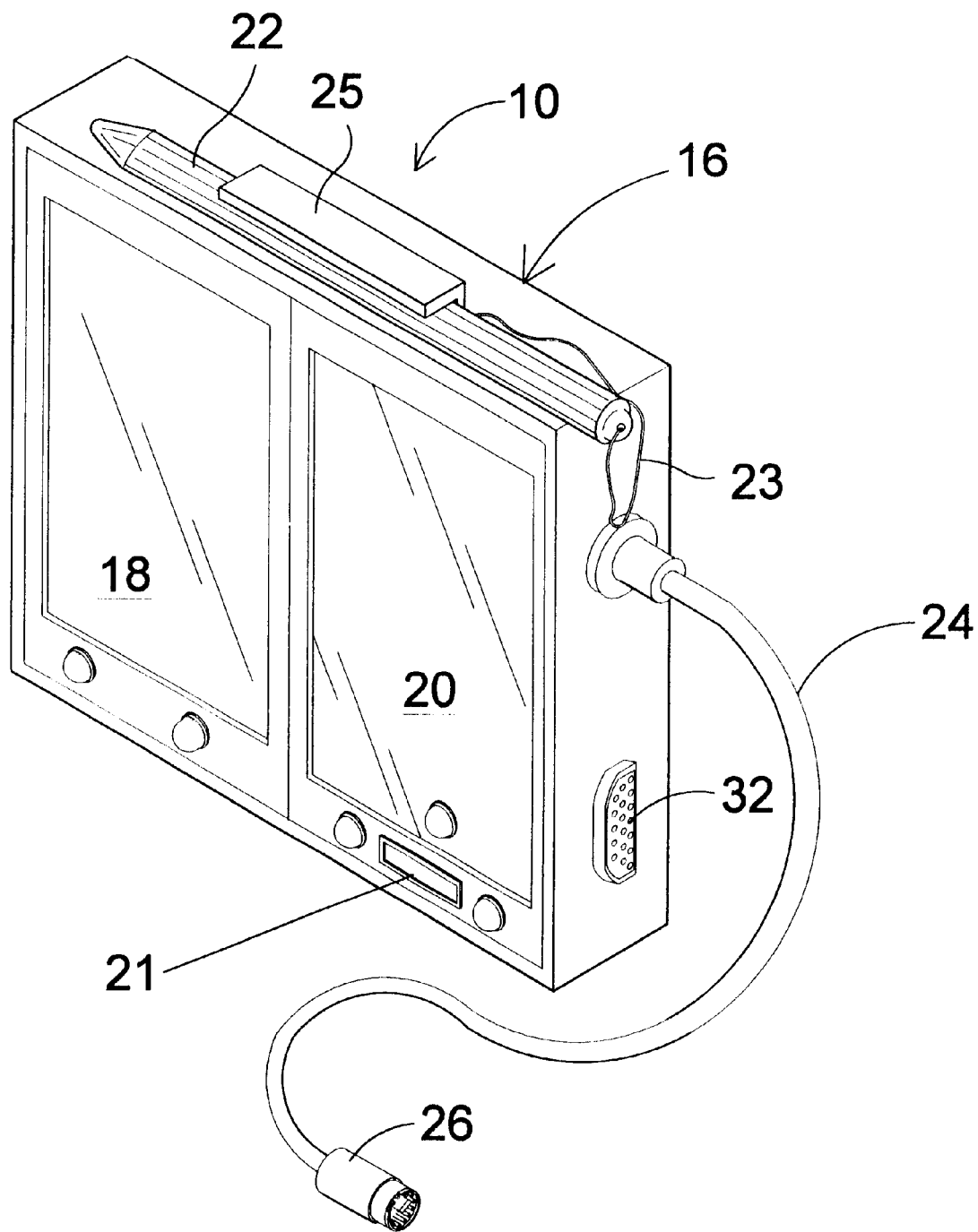
FIG. 2 is a top perspective view of the hand held medical examination device of the present invention.

An enlarged view of the computer 16 and cable wire 24 is illustrated in FIG. 2. As can be seen from this figure, the computer 16 is in an open operational position and the cable wire 24 is connected to extend from a side thereof. Positioned on a first side of the computer 16 are the image display screen 18 and the data display touch screen 20. A power switch 21 is also provided on the first side for connecting a power source within the computer 16 to a microprocessor which controls operation of the computer 16. Alternatively, a port for connection with an external power source such as an electrical outlet or a battery may be provided on a side of the computer 16. A stylus 22 is secured to the computer 16 by a cord 23 for use in inputting data to the computer 16 by touching the touch screen 20. A clip 25 is provided on a side of the computer 16 for receiving the stylus 22 when not in use. The computer 16 has a software program stored therein which will prompt the medical technician 12 to enter data using the stylus 22 according to a check list. The data input using the stylus 22 will be displayed on the data display touch screen 20. Connected to extend from a connection port on a side of the computer 16 is the cable wire 24. Extending through the cable wire 24 is a fiber optic camera which is able to capture images at which it is pointed and relay image data regarding the captured image to the computer for processing. At an end of the cable wire 24 opposite the connection to the computer 16 is the universal adapter 26. The universal adapter 26 is provided for connecting the cable wire 24 to any of a number of different medical devices. Connection of a medical device allows the fiber optic camera to view a body part seen through the medical device and thereby provide an image of the desired part of the patients body to the computer 16 for display on the image display screen 18.

Figure 3:
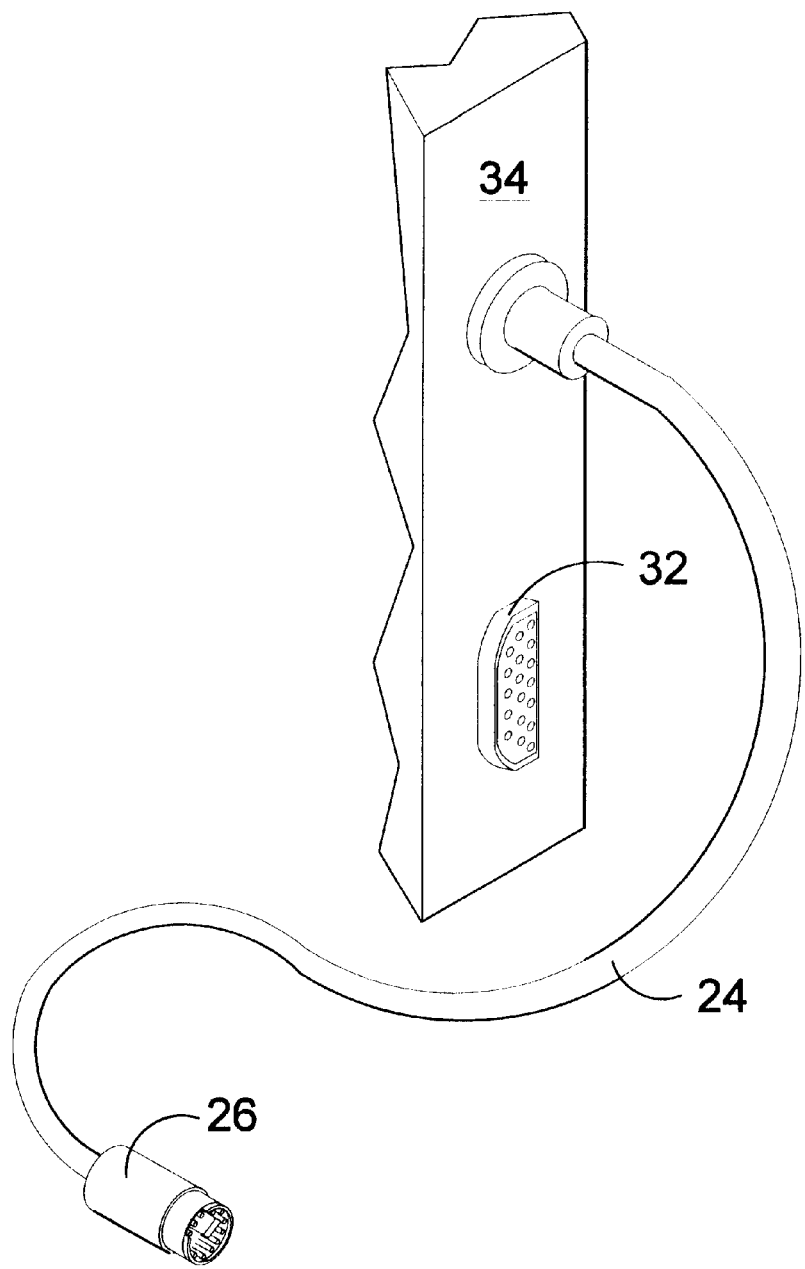
FIG. 3 is a side view of the hand held medical examination device of the present invention.
Figure 4:
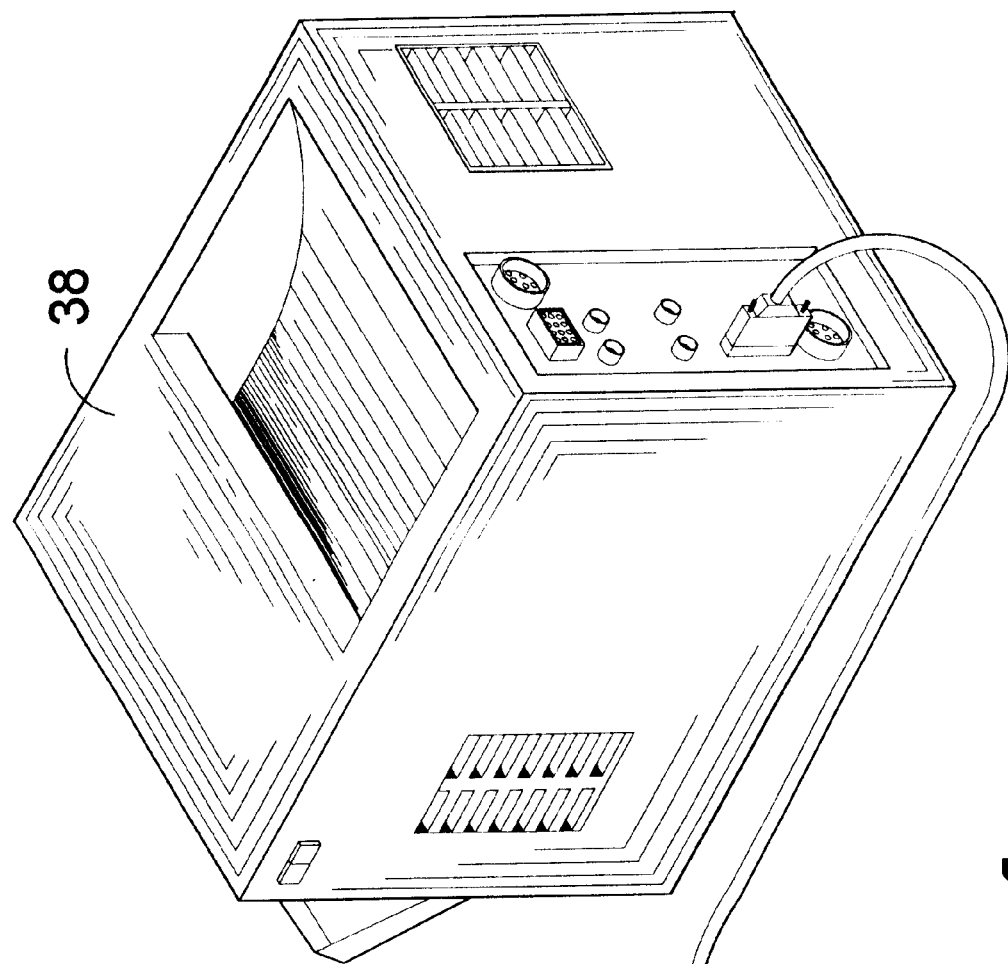
FIG. 4 is a top perspective view of the hand held medical examination device of the present invention connected to a printer for producing a hard copy of the medical data collected during an examination of a patient.

FIG. 3 illustrates a view of a first side 34 of the computer 16. Positioned on the first side 34 of the computer 16 is a connection port 35 for the cable wire 24. The cable wire 24 is connected to extend from the connection port 35 and is flexible allowing the medical technician to freely move the cable wire 24. Also positioned on the first side 34 is a connection port 32 for a peripheral device. FIG. 4 illustrates a connection wire 36 for connecting the connection port 32 to a printer 38. The connection of a printer 38 to the computer 16 through the connection port 32 allows the computer 16 to output data stored therein and produce a hard copy of the data.

While a preferred output device 38 for connection to the output port of the computer 16 is shown and described herein, those of ordinary skill in the art who have read this description will appreciate that there are numerous other structures for connection to the output port of the computer 16 and, therefore, as used herein the phrase "means for receiving data from or providing data to the computer" should be construed as including all such structures as long as they achieve the desired result of receiving data from or providing data to the computer, and therefore, that all such alternative mechanisms are to be considered as equivalent to the one described herein. Thus, any known peripheral device may be connected to the computer as long an appropriate connection wire is provided.

Figure 5:
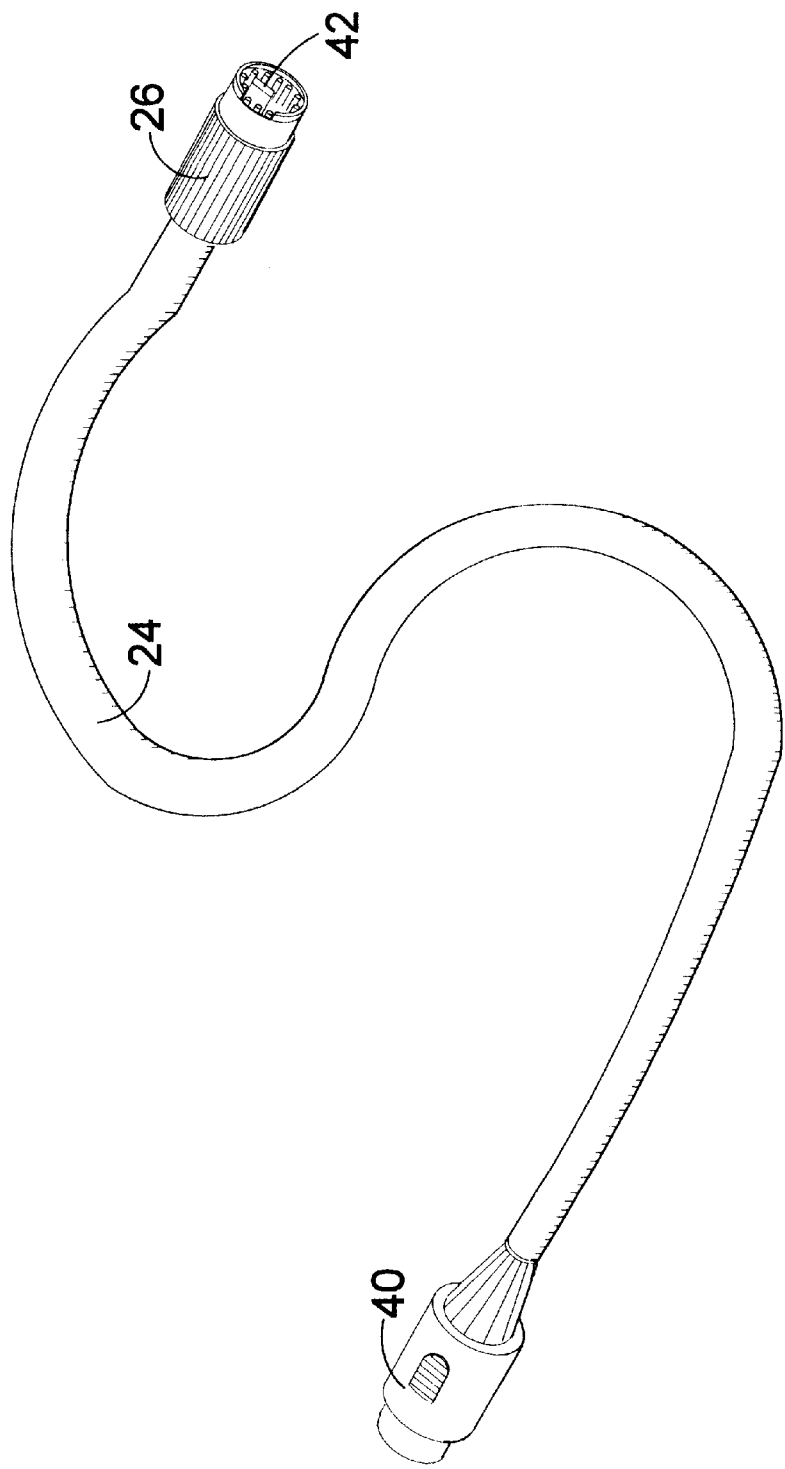
FIG. 5 is an enlarged view of the cable including a camera extending therethrough used with the hand held medical examination device of the present invention.

An enlarged view of the cable wire 24 is illustrated in FIG. 5. As can be seen from this figure, an adapter 40 is provided on one end of the cable wire 40 for connection to the computer 16 and a universal connector 26 is provided on an opposing end for connection to a medical device. The medical device will include an adapter thereon for allowing connection to the cable wire 24, Examples of medical devices including adapters are illustrated in FIGS. 6A–6D and will be described hereinafter. Extending through the cable wire 24 is a fiber optic camera 42 shown extending through an end of the cable wire at the universal adapter 26. Both the cable wire 24 and the fiber optic camera 42 are flexible and thus can be easily maneuvered when being used to perform a medical examination. When the cable wire 24 is connected to the computer 16 through the adapter 40, the fiber optic camera 42 will connect with a microprocessor within the computer 16 for supplying data indicative of the images captured thereby to the microprocessor.

Figure 6C:
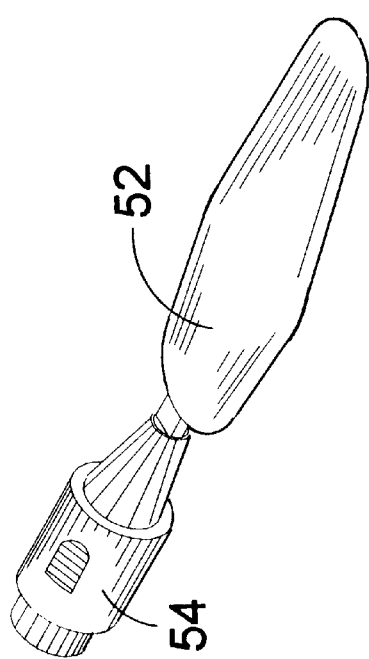
FIG. 6C is a perspective view of a tongue depressor which may be connected to the hand held medical examination device of the present invention.
Figure 6D:
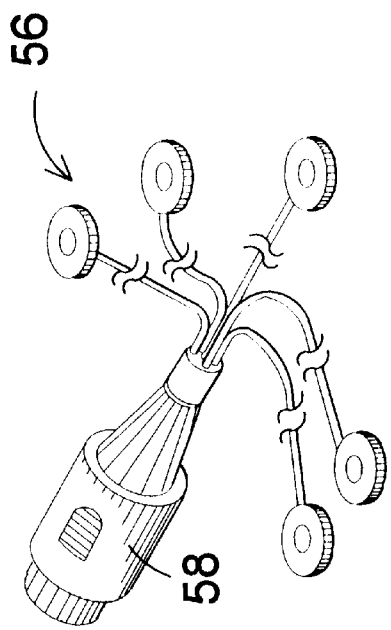
FIG. 6D is a perspective view of electrocardiogram probes which may be connected to the hand held medical examination device of the present invention.
Figure 6A:
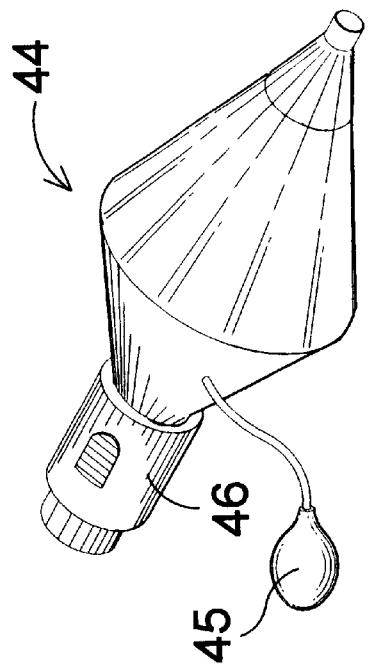
FIG. 6A is a perspective view of an ear piece which may be connected to the hand held medical examination device of the present invention.

A number of medical devices able to be connected to the universal adapter 26 are illustrated in FIGS. 6A–6D. An ear piece 44 is illustrated in FIG. 6A. Attached to one end of the ear piece 44 is an adapter 46 for connection to the universal adapter 26. The adapter 46 aligns the fiber optic camera 42 with the ear of a patient for capturing an image of the inside of the ear. Data regarding the captured image is provided to a microprocessor within the computer 16 for processing and display on the image display screen 18. This provides an enlarged image for a medical technician to view and analyze. A rubber bulb 45 is also provided to insufflate the ear drum. The pumping of air into the ear canal using the pump 45 will allow the technician to detect the motion of the ear drum.

Figure 6B:
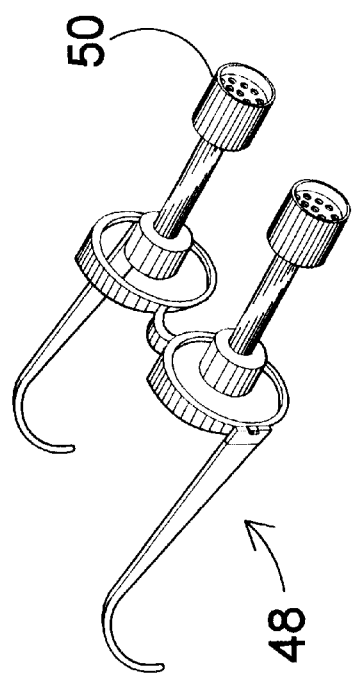
FIG. 6B is a perspective view of a pair of eye glasses which may be connected to the hand held medical examination device of the present invention.

A pair of eye glasses 48 is illustrated in FIG. 6B for use in examining an eye of a patient. Attached to one end of the pair of eye glasses 48 is an adapter 50 for connection to the universal adapter 26. The adapter 50 aligns the fiber optic camera 42 with the eyes of a patient for capturing an image of the eyes. Data regarding the captured image is provided to a microprocessor within the computer 16 for processing and display on the image display screen 18. This provides an enlarged image for a medical technician to view and analyze.

A tongue depressor 52 is illustrated in FIG. 6C for use in examining the mouth of a patient. Attached to one end of the tongue depressor 52 is an adapter 54 for connection to the universal adapter 26. The adapter 54 aligns the fiber optic camera 42 with the inside of the mouth of a patient for capturing an image of the mouth and throat of the patient. Data regarding the captured image is provided to a microprocessor within the computer 16 for processing and display on the image display screen 18. This provides an enlarged image for a medical technician to view and analyze.

Electrocardiogram probes 56 are illustrated in FIG. 6D for use in taking an EKG of a patient. Connected to the EKG probes 56 is an adapter 58 for connection to the universal adapter 26. The adapter 58 connects the EKG probes to the microcomputer for analysis thereby. Data regarding the results of the EKG are provided on the data display touch screen 20 for viewing and analysis by a medical technician.

Figure 7:
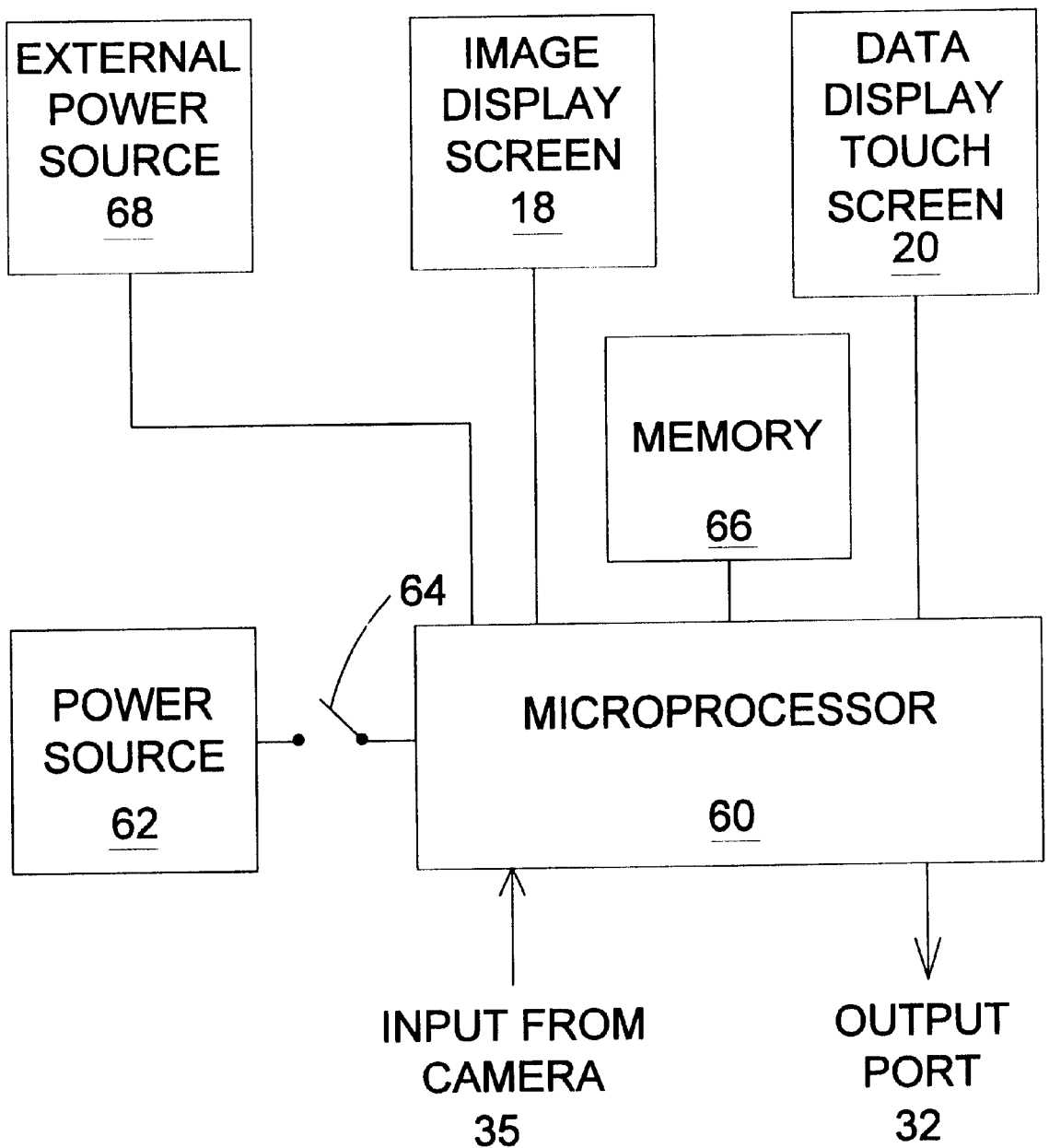
FIG. 7 is a block diagram of the computer of the hand held medical examination device of the present invention.

A block diagram of the computer is illustrated in FIG. 7. The computer includes a microprocessor 60. The microprocessor 60 is connected to a power source 62 via a power switch 64. A connection port 68 for connection to an external power source is also connected to the microprocessor 60 through the power switch 64. The data display touch screen 20 is also connected to the microprocessor 60 for use in inputting data to the microprocessor through contact with the screen such as by the stylus 22, display of the data input using the stylus and other data analyzed by the microprocessor 60 and related to a medical examination. The connection port 35 is connected to supply image and examination data accumulated by the medical devices connected to the cable wire 24. The image data provided by the fiber optic camera 42 is analyzed by the microprocessor 60 and provided for display on the image display screen 18. A memory 66 is also provided connected to the microprocessor 60 for storing data related to the medical examination and patient received from both the data display touch screen 20 and through the connection port 35. The memory 66 may store data from numerous different patients and thus compile a medical history of a number of patients. The memory will also store software programs which the microprocessor uses to prompt a technician using the hand held medical examination device 10 on the data display touch screen 20 to input data. The output port 32 is provided for connection of a peripheral device. The peripheral device will receive data from the microprocessor 60. Any type of peripheral device may be connected to receive data from the microprocessor 60 or provide data to the microprocessor 60. A printer may be connected to produce a hard copy of the data processed by the microprocessor 60. A disk drive, CD ROM drive or tape drive may be provided for copying data provided by the microprocessor 60 on to a storage medium. Any other type of peripheral device may be provided for performing any desired operation and connected to the output port 32 as long as a connection wire is provided.

The operation of the hand held medical examination device 10 will now be described with reference to the figures. In operation, the hand held medical examination device 10 is turned on by pressing the power button 21. Activating the power switch 21 will connect the microprocessor 60 to one of the internal power source 62 or external power source 68 applying power thereto. The application of power to the microprocessor 60 will turn on the computer and supply power to both the image and data display screens 18 and 20 and the keyboard 22. The cable wire 24 will be connected to the connection port 35 connecting the fiber optic camera 42 to the microprocessor 60. The connection of the fiber optic camera 42 to the microprocessor 60 will allow the application of power thereto through the connection port 35.

The medical technician performing the examination will now input data related to the patient using the data display touch screen 20 and stylus 22 according to prompts displayed on the touch screen 20. The prompts are displayed on the touch screen 20 in accordance with a software program stored in the memory 66. The prompts provide a check list for the technician through which data regarding the patient will be input. The data input through the touch screen 20 will be stored in the memory 66. The medical technician will now connect a first one of the medical devices to the universal adapter 26 and move the medical device into the proper position to examine the desired body part. The fiber optic camera 42 will capture an image of the desired body part and transmit the image data to the microprocessor 60 for processing. The processed image data will then be provided to the image display screen 18 generating an enlarged image of the desired body part for viewing and analysis by the medical technician. This will be repeated with each medical device until each desired body part is examined. As each body part is viewed on the image display screen 18, the medical technician can input data related to the viewed image through the data display touch screen 20.

Once the examination is complete, a peripheral device such as a printer or storage device, may be connected to the computer 16 through the output port 32 for transferring data between the peripheral device and the microprocessor 60. When a printer is connected to the output port 35, data from the microprocessor 60 may be provided for generation of a printout thereof which may be easily analyzed. When a storage device is connected to the output port 32, data may be provided from the microprocessor for storage on a storage medium.

From the above description it can be seen that the hand held medical examination device of the present invention is able to overcome the shortcomings of prior art devices by providing a hand held medical examination device which is able to connect with numerous medical devices for examining multiple body parts and store a plurality of medical histories and examinations whereby quick and easy physical examinations of patients in emergency rooms may be performed as patients wait to be seen. The hand held medical examination device includes a miniature camera connected to the computer through a connection port for displaying a body part being examined on a display screen, the numerous medical devices each connect to the computer through an adapter cable within which the fiber optic camera extends. Furthermore, the hand held medical examination device of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A hand held medical examinationn device comprising:
   a) a hand held computer during use including a microprocessor, a touch screen for inputting data to the microprocessor and displaying data, a display screen and only one connection port, said touch screen and said display screen being located side by side on a face of said hand held computer;
   b) only one cable wire connected to said microprocessor through said connection port including a universal adapter adapted to connect to any one of a plurality of medical devices used to perform a physical examination;
   c) a camera extending through said cable wire for capturing an image viewed through the medical device connected to said universal adapter and providing data related to said captured image to said microprocessor for processing and display on said display screen;
   d) said display screen displaying an image viewed by said camera; and
   e) a stylus for use in inputting data on said touch screen, said computer having stored within a software program to prompt a medical technician through said touch screen to enter data.

2. The hand held medical examination device as recited in claim 1, further comprising a memory unit connected to said microprocessor for storing data input from said touch screen and cameral related to a plurality of patients.

3. The hand held medical examination device as recited in claim 1, further comprising a peripheral device port for connecting said microprocessor to a peripheral device.

4. The hand held medical examination device as recited in claim 3, wherein said peripheral device is a printer for generating a printout of data related to a medical history of a patient being examined.

5. The hand held medical examination device as recited in claim 1, wherein said plurality of medical devices include an ear piece, a pair of eye glasses, a tongue depressor and electrocardiogram probes.

6. The hand held medical examination device as recited in claim 5, wherein said ear piece directs said camera at an inner side of an ear of a patient, thereby allowing an image of the inner eat of the patient to be captured thereby.

7. The hand held medical examination device as recited in claim 6, wherein said ear piece includes a pump for insufflating an ear drum of the patient and thereby allowing detection of a motion of the ear drum.

8. The hand held medical examination device as recited in claim 5, wherein said pair of eye glasses direct said camera at an eye of a patient, thereby allowing an image of the eye of the patient to be captured thereby.

9. The hand held medical examination device as recited in claim 5, wherein said tongue depressor directs said camera within the mouth of a patient, thereby allowing an image of the mouth and throat of the patient to be captured thereby.

10. The hand held medical examination device as recited in claim 5, wherein each of said ear piece, pair of eye glasses, tongue depressor and electrocardiogram probes include an adapter for connection with said universal adapter.

11. The hand held medical examination device as recited in claim 10, wherein said data related to the electrocardiogram examination of the patient transmitted to said microprocessor is displayed on said display screen.

12. The method of conducting a physical examination comprising the steps of:
   a) deploying a hand held computer, said computer comprising a microprocessor, a touch screen for inputting data to the microprocessor and displaying data, a display screen next to said touch screen, only one connection port, only one cable wire connected to said microprocessor through said connection port including a universal adapter for use with any one of a plurality of medical devices used to perform a physical examination, a camera extending through said cable wire for capturing an image viewed a medical device connected to said universal adapter, said camera capturing an image for display on said display screen;
   b) using a stylus to input data on said touch screen; and
   c) said touch screen prompting a medical technician to enter said data according to a check list displayed on said touch screen.

* * * * *